United States Patent [19]

Winslow, Jr.

[11] 3,936,729
[45] Feb. 3, 1976

[54] CONDUCTIVITY MEASUREMENT PROBE

[75] Inventor: Joseph D. Winslow, Jr., Houston, Tex.

[73] Assignee: Petrolite Corporation, St. Louis, Mo.

[22] Filed: Feb. 28, 1974

[21] Appl. No.: 446,854

[52] U.S. Cl............ 324/30 B; 73/194 E; 204/195 F
[51] Int. Cl.²......................................... G01N 27/42
[58] Field of Search................. 324/30 R, 30 B, 64; 73/194 E; 204/195 F, 195 R

[56] References Cited
UNITED STATES PATENTS

| | | | |
|---|---|---|---|
| 2,871,445 | 1/1959 | Carter | 324/64 |
| 2,964,941 | 12/1960 | Marsh | 324/30 B |
| 3,250,987 | 5/1966 | Okada | 324/30 B |
| 3,458,421 | 7/1969 | Dahms | 204/195 F |
| 3,732,159 | 5/1973 | Platt | 204/195 R |

*Primary Examiner*—R. V. Rolinec
*Assistant Examiner*—Michael J. Tokar
*Attorney, Agent, or Firm*—Emil J. Bednar

[57] ABSTRACT

A conductivity measurement probe formed of an electrically nonconducting rigid body which carries a cylindrical flow passage defining a flux channel to polarization current. The body has inlet and outlet means for passing aqueous liquid or other electrolytes through the flow passage. Four elongated metallic electrodes are positioned in alignment within the flow passage and in electric isolation from one another. Preferably, the outer electrodes serve as references for observing induced polarizing potential and an inner pair of the electrodes which serve auxiliary functions for providing current flow in the flow passage; and, the reference electrodes reside within the limits of the flux channel containing the polarization current. The reference and auxiliary electrodes are preferably spaced uniformly along the flow passage. Electrically conductive means extend from the electrodes within the body. These conductive means are insulated from one another and the body to form circuits through the electrodes during conductivity measurements.

10 Claims, 5 Drawing Figures

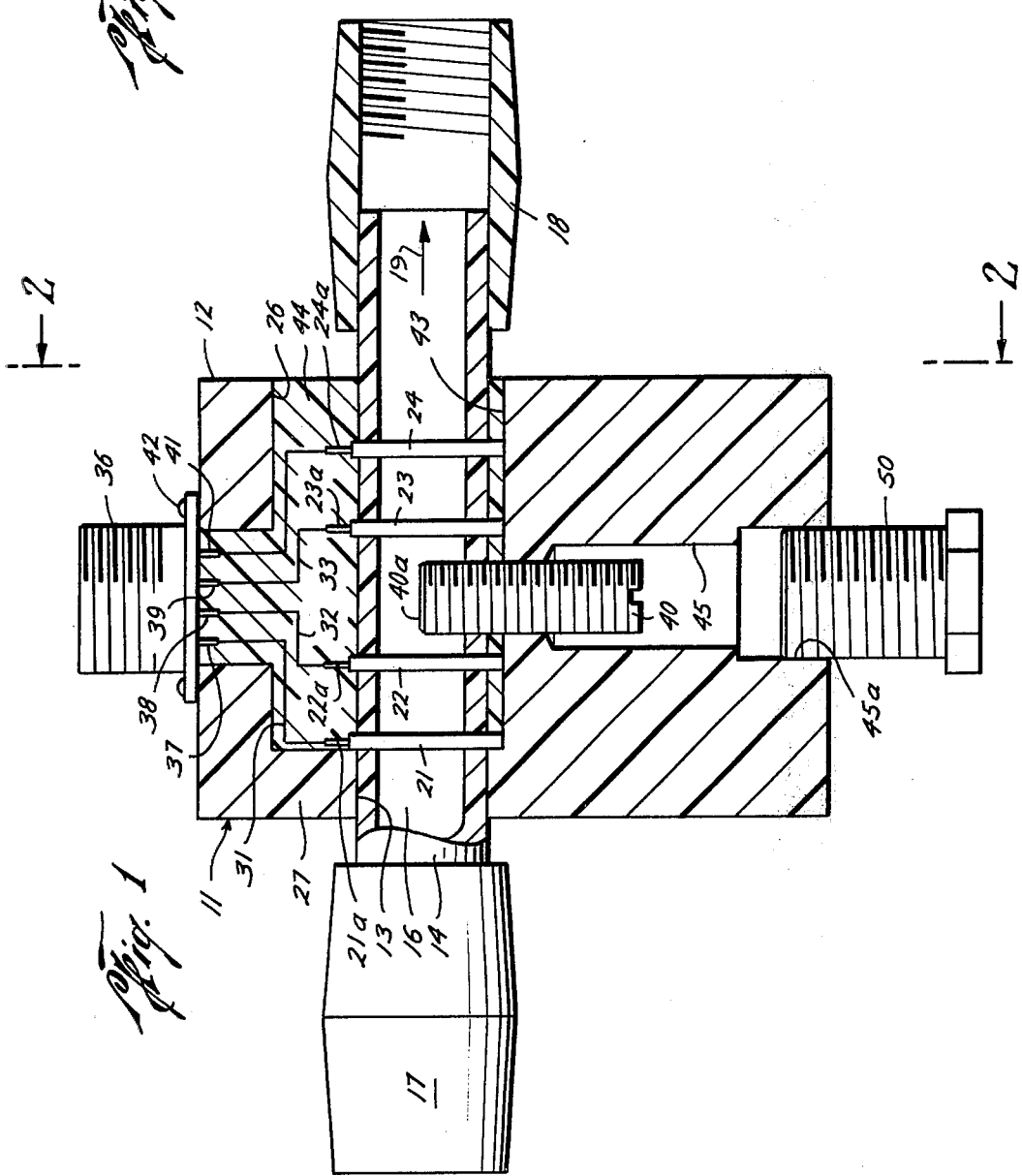

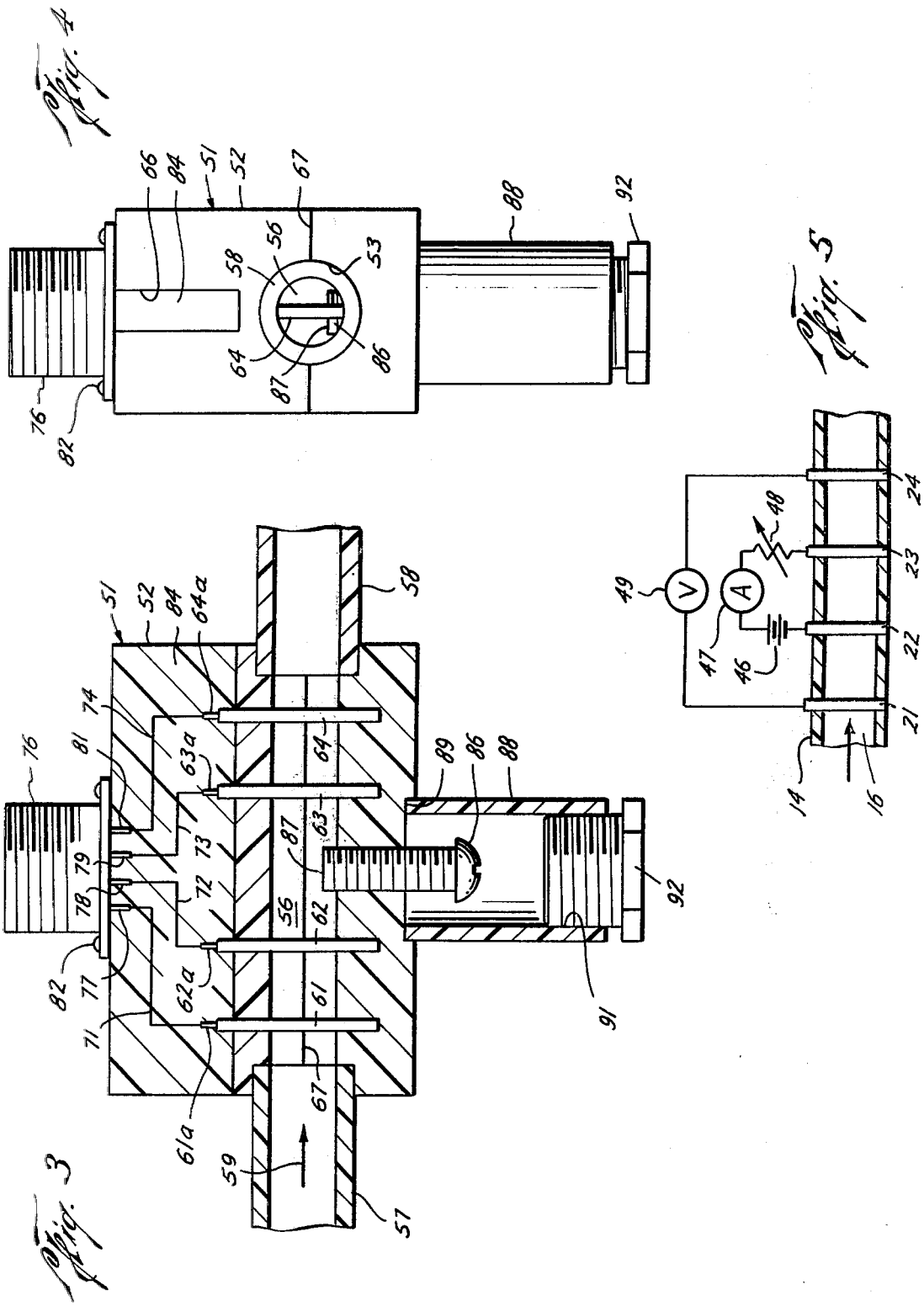

CONDUCTIVITY MEASUREMENT PROBE

BACKGROUND OF THE INVENTION

1. Field of the Invention

This invention relates generally to the measurement of electrical conductivity of a liquid, and particularly, it concerns an improved conductivity probe for use with electrical conductivity measuring instruments.

2. Description of the Prior Art

The determination of the conductivity of an electrolyte such as an aqueous liquid has been an elusive task for over one hundred years. A multitude of techniques and apparatuses were tested before relatively satisfactory systems were found for this purpose. The greatest error in prior attempts to measure electrolytic conductivity were caused by the polarization of electrodes which were employed for potential sensing and current source purposes. Attempts to avoid the problem with the polarization of electrodes resulted in two separate electrical systems being developed for measurement of conductivity.

The polarization of electrodes can be eliminated by using alternating current of relatively high frequency and stability combined with very special electrodes coated with platinum black. These electrodes expose a large surface to an electrolyte so as to reduce the surface density of ions being deposited and thereby reducing the polarization effects.

The use of d.c. measurement system for determining conductivity has several advantages, the principal advantage being in avoiding a precisely settable and stable high frequency oscillator for generating the alternating currents of the preceding a.c. measurement system. Many attempts were made to employ d.c. currents for the measurement of conductivity of aqueous liquids and other electrolytes. Nearly one hundred years ago, a method was developed in which the polarization effects of electrodes could be reduced to manageable proportions for producing reliable conductivity measurements. In such a method, a constant current is passed through the electrolyte and the drop in potential between two points in the system is measured by secondary electrodes connected to an electrometer.

The use of such a plurality of electrodes implements a novel technique where current flow between a first set of electrodes creates a polarization potential between an additional set of potential monitoring electrodes. In such arrangement, the change in current can be correlated to the change of polarization potential at the reference electrodes. Thus, such measurements can be correlated directly to the electromotive force which opposes the flow of current through the electrolyte. The problem of polarization at the electrodes can be overcome by applying a small finite current flow and measuring the induced polarization potential change. Pursuant to Ohm's Law, the smallest polarization potential change is induced by a corresponding current flow. The original polarization potential at the measurement electrodes is eliminated in a linear system. Now, the measurement system follows Ohm's Law, the polarization potential about the measurement electrodes and the current flow inducing same are directly proportional and simultaneously approach zero magnitudes.

In many of the known direct current measurement systems for determining conductivity of electrolytes, the measurement is made in what is termed an "open" cell. The electrodes are immersed within a liquid, but the system is exposed to atmospheric and other external forces, which forces undesirably effect the current flow between the electrodes. Thus, movement of the electrodes relative to the container, the placement into the solution of some foreign material such as an air bubble, and stirring or like mechanical displacement, severely affected the accuracy of these d.c. measurements with electrodes in an open cell.

Complicated conductivity probe design may be employed with "closed" cells in which the conduction path for the electric current between a pair of electrodes is confined to a fixed volume of liquid within the completely enclosed nonconductive structure to avoid external interference forces. However, such probe designs are substantially affected by liquids carrying solids which deposited within the confined areas of the probe. As the solids and other deleterious materials become entrapped in these complex probes, the calibration accuracy of the probes begin to vary thereby affecting the conductivity measurement. Repeated standardizations and recalibrations or cleaning of the probe are required to maintain accurate measurements.

The present invention is a conductivity measurement probe of the closed cell type, but one which has a relatively simple design for confining the current flux within a channel and with such electrode configuration that the calibration constant of the probe is substantially determined only by the physical dimensions of the flux channel and electrode spacing and not by the surface area, size, shape or corrosion and scaling of the electrodes.

SUMMARY OF THE INVENTION

In accordance with this invention, there is provided a conductivity probe having a rigid body. A cylindrical flow passageway is formed within the body having electrically nonconductive wall members thereby producing an insulated boundary defining a flux channel to polarizing current. Inlet and outlet means pass aqueous liquid through the flow passage. Four metallic electrodes of elongated configuration are disposed in the flow passage and are positioned in parallel relationship with their longitudinal axis transverse to the flow passage. These electrodes all reside in a plane containing a longitudinal axis of the flow passage and they are electrically isolated from the body. One pair of these electrodes are auxiliary electrodes for providing current flow in the flow passage. Another pair of these electrodes are reference electrodes which monitor polarization potential. The auxiliary electrodes may reside adjacent one another and the reference electrodes may reside remote to one aanother at the limits of the flux channel and adjacent to each of the auxiliary electrodes. Preferably, each reference electrode is spaced equidistantly from the adjacent auxiliary electrode, and the auxiliary electrodes are spaced apart a greater distance from one another than from the reference electrode. Electrically conductive means extend from the auxiliary and reference electrodes within the body. The conductivity means are insulated from one another and from the body so that the conductivity means form circuits through the electrodes during conductivity measurement.

BRIEF DESCRIPTION OF THE DRAWINGS

FIG. 1 is a vertical section (partial) through a first embodiment of the conductivity probe of this invention;

FIG. 2 is an end view of the conductivity probe shown in FIG. 1;

FIG. 3 is a vertical section (partial) through a second embodiment of the conductivity probe of this invention;

FIG. 4 is an end view of the conductivity probe of FIG. 3 taken along line 3—3; and FIG. 5 is an illustrative schematic circuit of the method of employing the conductivity probe shown in the preceding figures according to the present invention.

DESCRIPTION OF SPECIFIC EMBODIMENTS

In the drawings there are illustrated two embodiments of the conductivity probe of the present invention. Both of these conductivity measurement probes encompass all of the advantages of the present invention, but one may be more suitable for manufacture in one form or the other depending on the particular circumstances of the user. In FIGS. 1 and 2 there is shown a first embodiment of a conductivity measurement probe 11 which is formed of a rectangular body 12 of a rigid material. This material may be a polymerized plastic such as polyvinyl chloride. Other materials may be employed for constructing the body 12, but preferably they are selected from electrically nonconducting plastics. The body 12 is provided with an axial opening 13 of cylindrical configuration which extends through the body 12. Although the surrounding portions of the body 12 may form electrically nonconducting wall members, it is preferred to insert a tubular member 14 into the opening 13 to form a cylindrical flow passageway 16 through the body 12. The tubular member 14 is preferably formed of a compatible material to the body 12 and polyvinyl chloride pipe of suitable dimensions is expecially suitable for this purpose. Where this material is employed, an adhesive may be employed within the opening 13 so that the body 12 and tubular member 14 are integrally secured into a unitary structure. As a result, the passageway 16 extends through the body 12 and forms the flux channel to polarizing current which is to be established between electrodes contained therein. The tubular member 14 has an inlet coupling 17 and an outlet coupling 18 by which connection to an external source may be made so that the electrolyte or aqueous liquid may be passed through the passageway 16 in the direction indicated by the arrow 19. However, the inlet and outlet couplings may be reversed so that the fluid may be passed through the passageway 16 in the reverse direction. The probe 11 is symmetrical to flow of current and therefore it is immune to the directional flow of liquid or current affecting conductivity measurements.

Four metallic electrodes 21, 22, 23, and 24 which have an elongated configuration are disposed in the passageway 16. These electrodes may take any suitable form, but preferably are substantially identical cylindrical members. However, they need not be identical for purposes of the present invention. Identical cylindrical electrodes are preferred for purposes of construction. For ease in construction, the electrodes are disposed symmetrically within the passageway 16. In addition, the electrodes are positioned in parallel side-by-side relationship and reside with their longitudinal axis transverse to the passageway 16. Additionally, these electrodes reside in a plane containing the longitudinal axis of the passageway 16. The electrodes may be mounted within the probe 11 by any suitable means, such as with an adhesive, but they are electrically isolated from the body 12.

Although the electrodes are illustrated as traversing the wall members of the tubular member 14, such arrangement is not necessary. The electrodes need only to be mounted so that they extend transversely into the passageway 16. However, for purposes of convenient construction, the tubular member 14 is formed with aligned openings through its wall members to receive the electrodes. Each electrode carries an end member 21a, 22a, 23a, and 24a, respectively, by which electrical conductors may be secured to them. In order to accommodate such a relationship, the body 12 is relieved to provide an opening into which internal pieces may be received. This opening may be provided by a second axial opening 26 formed coaxially with the opening 13. The axial opening 26 need not extend through the body 12, but may be terminated a short distance from one end thereby forming an impermeable wall portion 27 adjacent the electrode 21. Preferably, the electrodes are mounted within the tubular member 14 in the mentioned openings prior to mounting the tubular member 14 within the body 12. Also, it is desirable before this assembly that the electrical conductors 31, 32, 33, and 34 be secured to the end portions 21a, 22a, 23a, and 24a, respectively. After the tubular memer 14 is inserted within the body 12 and secured thereto, these electrical conductors connect to an external electrical fitting 36 of any suitable type such as a female multiterminal plug to receive an external shielded and waterproof cable. The conductors are secured, such as by soldering, to terminal pins 37, 38, 39, and 41 of the connector 36. The connector 36 is secured, preferably in watertight interconnection, to the body 12 by screws 42.

After assembly of the electrical fitting 36 upon the body 12, the opening 26 is filled to a substantially void-free environment with a nonconducting potting material. The potting material can be a polyvinyl chloride compatible resin with suitable plasticizer forming a liquid mixture that can be poured into the opening 26 with the tubular member upright having the outlet coupling 18 superimposed. With time passage, the liquid mixture sets into an impermeable, electrically nonconducting solid material 44 substantially of the same rigidity as the body 12. For example, the potting material can be R-826 Liquid Resin from the Ring Chemical Company of Houston, Texas, and a setting catalyst such as Versamid 140 which is a polyamide castable plastic catalyst. The potting material hardens and unites the described elements into a unitary conductivity measurement probe 11 which is substantially sealed to any leakage of fluid about the electrodes through the wall members of the tubular member 14 into the body 12. If desired, the opening 13 may be enlarged slightly coextensively with opening 26 so that the potting material 44 completely surrounds the entire tubular member 14 where it traverses the body 12. Thus, an opening 43 about the tubular member 14 is also filled with the potting material 44.

The electrodes are positioned in a symmetrical arrangement within the body 12. The electrodes 21 and 24, or 22 and 23, may be either reference or auxiliary electrodes. However, best results are obtained with electrodes 21 and 24 being references and electrodes 22 and 23 serving the auxiliary function. In the probe 11, the electrodes 22 and 23 are auxiliary electrodes for providing current flow in the passageway 16. The electrodes 21 and 24 are reference electrodes for monitoring the polarization potential therebetween which is induced by the current flow between the auxiliary electrodes 22 and 23. The reference electrodes should be spaced at least three diameters from the adjacent auxiliary electrode so that the electrodes 21 and 24 are beyond the current paths about the auxiliary electrodes 22 and 23. As a result, the boundary films about the reference electrodes 21 and 24 are not disrupted. Since the passageway 16 is circumferentially enclosed by insulating material and current cannot pass beyond the outer electrode pair, this structure delimits the electrodes into a well defined flux channel. Improved results are obtained with the auxiliary electrodes 22 and 23 spaced a distance greater than twice the spacing between any of the auxiliary and reference electrodes. With this arrangement, the reference electrodes are in the shadow of auxiliary electrodes beyond current flows. Thus, the electrodes 21 and 24 are "shielded" from stray currents. This effect is likened to a shadow about the reference electrodes where the lack of light is lack of current flow from the auxiliary electrodes to the reference electrodes.

As has been mentioned, the construction, cross-sectional area, and other physical size parameters of the electrodes do not influence the operability or the calibration of the probe 11 except in the second order relationship. Since the passageway 16 is cylindrical and the electrodes are mounted therein in a symmetrical relationship, the calibration constant for the conductivity measurement probe 11 is substantially determined only in the first order by the spacing between the electrodes 22 and 23 relative to the cross-sectional area (in a transverse plane) of the passageway 16. The effect of electrode size (diameter and length), corrosion attack and incomplete scale coverage of electrodes are only third order effects. Thus, corrosion, pitting and other physical changes in the electrodes do not affect the calibration constant for the probe 11. Should the mentioned ratios concerning the flux channel and inner electrode pair spacings within the passageway 16 be changed, then and only then, will the calibration constant change. Since the possibility of changing the length of the flux channel within the passageway 16 during use is relatively impossible, the probe 11 is of the "closed" cell type so that external influences about the probe 11 do not interfere with the conductivity measurement being undertaken. Also, any change of the cross-sectional area of the flow passageway 16 can only occur by deposition of solids therein. Usually, such deposition is of uniform dimension throughout the circumference and length of the passageway 16. Thus, the influence upon the cross-sectional ratio factor determining the conductivity probe's cell constant is very minute. Thus, the probe 11 maintains a cell constant for most practically any environmental use until the electrodes are completely destroyed by corrosion or other physical reduction to an inoperative size, namely, disappearance.

The determination of the calibration constant for the corrosion measurement probe of the present invention is determined by unique relationship of mathematical definition for the probe employed therein. More particularly, these probes are defined by the following relationship: $i = v(A/d)1/e$ wherein $i$ is the current between the auxiliary electrodes, $v$ is the incremental change in polarization potential between the reference electrodes, $e$ is the resistivity of the electrolyte (e.g., water), $A$ is the cross-sectional area of the passageway 16, and $d$ is the distance between the auxiliary electrodes 22 and 23. Since $A$ and $d$ are fixed in relationship, then $i = v(K/e)$ wherein $K$ is the "cell" constant. Rewriting the equation for the system $i/v = K/e = K\Delta$ wherein $\Delta$ is the conductivity of the electrolyte. Since $i$ and $v$ are readily measured, the conductivity is easily found when $v$ is near zero, $i = K'\Delta$ since $K'$ is the system calibration constant pursuant to Ohm's Law.

The conductivity measurement probe 11 can be manufactured to an exactly precise calibration constant. However, the expense of such technique of manufacture need not be suffered. For this purpose, the probe 11 is provided with a very unique method of adjusting the system calibration constant $K'$ to a particular desired value and especially to a calibration with a particular external associated electrical system. For example, in the equation $i = K'\Delta$, a one micorampere can be equivalent to a conductivity of 1,000 micromhos where $K' = 0.001$ (approximately). For this purpose, the probe 11 is constructed with a system calibration constant K which is smaller than the desired value. Then, the probe 11 is connected through the electrical fitting 36 to an external electrical system. Current is passed through a known conductivity liquid between the electrodes 22 and 23 and the incremental change in polarization potential is measured through the electrodes 21 and 24. By the relatively simple earlier described calculation, the system calibration constant K' for the probe 11 can be determined.

For the purpose of determining K' and conductivity measurements, the circuit shown in FIG. 5 can be employed. In particular, the characteristics of the probe 11 are shown schematically in FIG. 5 and like parts have like reference numerals. A suitable current source, such as a battery 46, is placed in series with an ammeter 47 (e.g., a 0–500 micrometer) and a rheostat 48. By this means, a current flow is established between the electrode 22 and 23 with a suitable known electrolyte in the passageway 16. The electrolyte may be contained in a static environment or in a flowing condition. The particular flow state is immaterial to the operation of the probe 11. For example, the electrolyte may be distilled and gas-free water which has a known conductivity. The potential induced between the electrodes 21 and 24 is measured by a suitable high impedance voltmeter 49 (e.g., a 0–50 millivoltmeter). The instrumentation described in U.S. Pat. No. 3,717,566 may be employed for this purpose to good advantage. With this equipment, sufficient current is passed between the electrodes 22 and 23 so that there is about a 10 millivolt polarization potential change between the electrodes 21 and 24.

Should the cell constant K' be within the desired range with this particular instrumentation, the characteristics of the flux channel within the probe 11 can be adjusted for any specific calibration cell constant. For this purpose, an insulating member is mounted within the body 12 so that it may move transversely within the passageway 16 at a location substantially equidistantly from the auxiliary electrodes 22 and 23. Although the insulating member may be of any suitable form, it is preferred that the insulating member is threadedly mounted so that precise transverse movement within the passageway 16 may be obtained. For this purpose, the insulating member may be a screw 40 constructed of plastic material such as Nylon or polyvinyl chloride. The screw 40 is threaded through the body 12, the wall member of tubular member 14, and any intervening potting material 44. Adjustment of the screw 40 moves its end 40a transversely within the passageway 16. The movement of the screw between positions influences the cross-sectional area of the flux channel to current passages between the electrodes 22 and 23. By deflection of the lines of force which such current follows, the conductivity cell constant of the probe 11 can be adjusted to any precise value within a reasonable range. Once the screw 40 is adjusted, the probe 11 will remain within calibration. If desired, the screw 40 is received within a cylindrical cavity 45 in the body 12. The remote end of the cavity 45 carries an internal threaded portion 45a in which a threaded plastic plug 50 is received. As a result, fluids cannot move between the exterior environment into contact with the screw 40, nor to possibly enter the passageway 16. As a result, the probe 11 is substantially secured against the influences of external material which might influence the conductivity measurement.

Referring now to FIGS. 3 and 4, there is shown another embodiment of the present conductivity measurement probe which employs a flow passageway including electrodes forming a bounded flux channel so that the system constant K' of the probe is first order independent of the ratio of the length of the flux channel, electrode dimensions, etc. However, this embodiment has construction features which are desirable where the probe is to be inserted directly into an existing polyvinyl chloride piping system carrying the electrolyte. The conductivity measurement probe 51 is formed of a rigid body 52 which may be of any suitable material. Preferably the body 52 is formed of polyvinyl chloride plastic material. The body 52 may be rectangular in configuration and carries a cylindrical opening 53. The opening 53 has electrically nonconducting wall members which may be provided by the body 52 when constructed of a rigid plastic, nonconducting material. The cylindrical opening 53 forms a cylindrical passageway 56 which extends through the body 52. A pair of pipe segments 57 and 58 of the existing piping system serves as inlets and outlets for passing aqueous liquid through the passageway 56. The pipe segments are secured within the body 52 by an adhesive or other means. If desired, the functions of the pipe segments 57 and 58 may be reversed. Since the probe 51 is symmetrical relative to the conductivity measuring portions, fluid can be introduced into the passageway 56 in the direction indicated by the arrow 59 with equal facility and results as with flow in the reverse direction.

Four elongated metallic electrodes 61, 62, 63, and 64 are disposed transversely within the passageway 56 and positioned in a parallel relationship with their longitudinal axis. These electrodes reside in a plane containing the longitudinal axis of the cylindrical passageway 56 and are electrically isolated from the body 51. The dimensions and other criteria of the electrodes can be the same as has been described for probe 11 in the preceding embodiment.

In order to facilitate construction of the probe 51, the body is made in upper and lower halves joined at meeting surface 67 with a polyvinyl chloride cement. The body 52 has a rectangular opening 66 which permits aligned holes to be prepared in the opposite sidewall surfaces surrounding the passageway 56 within the body 52. The electrodes are received in fluid-tight engagement within these holes. The electrodes may extend completely through the passageway 56, or only partially therethrough, without detracting from the advantageous characteristics of the probe 51. The electrodes carry at their upper extremities (as illustrated in FIG. 3), end parts 61a, 62a, 63a, and 64a to which are secured electrical conductors 71, 72, 73, and 74. These electrical conductors extend from the electrodes to an external electrical fitting 76 carried on the exterior of the body 52.

The electrical fitting 76 may be of any conventional type such as a female screwed cap connector for a waterproof electrical cable attachment to the probe 51. In this regard, the electrical fitting 76 carries terminal pins 77, 78, 79, and 81 to which the electrical conductors 71, 72, 73, and 74, respectively, are connected. The electrical fitting 76 can be secured to the body 52 by screws 82 or other suitable fasteners. After the electrical conductors are secured between the electrodes and the terminal pins of the electrical fitting 76, the opening 66 is filled with any suitable potting compound 84. This compound may be of the same type of plastic material and catalyst described for the previous embodiment. End molding pieces (not shown) may close the sides of opening 66 so that the liquid potting compound fills the body 52 to substantially void-free completeness. After the potting compound has set to a state of rigidity, the exposed parts of the electrodes, the electrical conductors and the terminal pins of electrical fitting 76 are contained in a fluid-tight environment so that no fluids pass between the passageway 56 and the external portions of the body 52.

Although the probe 52 could be constructed to an exact conductivity cell constant K' (e.g., 1 milliampere = 1,000 micromhos), it may be desirable, as in the preceding embodiment to provide an insulating member which can transversely be moved within the passageway 56. For this purpose, an insulating member, such as a plastic screw 86, is positioned for transverse movement into the passageway 56 at an equal spacing from the electrodes 62 and 63. The screw 86 is adjusted by moving its end 87 within the passageway 56 until the system constant K' of the probe 51 is at the conductivity of a standard electrolyte solution which fills the passageway 56. The screw 86 is protected against accidental movement or injury by a plastic nipple 88 carried within a recess 89 formed in the body 52. The nipple 88 is secured within the recess 89 by an adhesive such as polyvinyl chloride cement. The nipple 88 carries internal threads 91 to receive a plastic plug 92.

The characteristics of the electrodes and their spacing within the probe 51 is identical to that described third the probe 11 in the preceding unit embodiments. The electrodes 62 and 63 are auxiliary electrodes for passing current through the electrolyte in the passageway 56. The reference electrodes 61 and 64 are placed at a position without the polarization currents. Therefore, the electrodes 61 and 64 and the passageway 56 define the extremities of the flux channel. The elelctrodes 61 and 62, and 63 and 64, should be at an equal spacing, whereas the electrodes 62 and 63 should be at a spacing greater than between the adjacent reference and auxiliary electrodes. Preferably, spacing between the electrodes 62 and 63 is twice that between the auxiliary and reference electrodes.

The probe 51 is employed in the same manner as the probe 11 of FIG. 1. The probe 51 connects to a suitable external circuit, such as schematically illustrated in FIG. 5, and current is passed between the electrodes 62 and 63 causing a predetermined shift in polarizing potential between the electrodes 61 and 64. The previously mentioned formula is employed for detemining the conductivity of the electrolyte contained within the passageway 56. The passageway 56 may be filled with a known electrolyte having a known conductivity. The response of the probe 51 is then determined, the screw 86 adjusted until the desired cell calibration constant is obtained, and plug 92 reinstalled. Thus, the probe 51 can be brought to any desired calibration relative to the ammeter 47 illustrated in FIG. 5.

From the foreging there has been described two embodiments of a probe of the present invention in which the conductivity is a function only of the distance between the auxiliary electrodes and physical dimensions of the flux channel provided therein. The dimensions, corrosion attack, pitting, fouling of the electrodes, including their shapes, size and surface areas have only a third order effect upon the measurement of conductivity. The probes have all the advantages of "closed" cell d.c. measurement systems of conductivity and are not influenced by the deposition of scale other than would severely change the dimension of the flux channel.

Various modifications and alterations in the described probe will be apparent to those skilled in the art from the foregoing description which do not depart from the spirit of the invention. For this reason, these changes in structure are desired to be included within the scope of the present invention. The appended claims define the present invention; the foregoing description is to be employed for setting forth the present embodiments as illustrative in nature.

What is claimed is:

1. A conductivity probe comprising:
   a. a body formed of a rigid insulating material and having a cylindrical opening therethrough;
   b. a tubular electrically nonconducting member positioned coaxially within said opening of said body with an annulus therebetween extending at least partially through said body and said tubular member forming a cylindrical flow passage within said body thereby providing an insulated boundary defining a flux channel to polarization current;
   c. said tubular member extending beyond the exterior surface of said body and carrying end connections adapted to function as inlet and outlet means for passing aqueous liquid through said flow passage;
   d. four metallic electrodes of elongated configuration disposed in the flow passage and mounted with at least one of their ends penetrating the wall of said tubular member within said annulus between said body and said tubular member, and said electrodes positioned in parallel relationship with their longitudinal axes transverse to said flow passage and residing in a plane containing the longitudinal axis of said flow passage;
   e. one pair of said electrodes being auxiliary electrodes for providing current flow in said flow passage and another pair of said electrodes being reference electrodes serving as polarization potential monitors, said auxiliary electrodes residing adjacent one another and said reference electrodes residing remote from one another at the limits of said flux channel and adjacent each auxiliary electrode;
   f. each of said reference electrodes spaced equidistantly from the adjacent auxiliary electrode, and said auxiliary electrodes spaced apart a greater distance from one another than said auxiliary electrodes from said reference electrodes;
   g. an elongated opening provided in said body intersecting said annulus and said elongated opening disposed in juxtaposition with said tubular member with one end of said electrodes being exposed by said elongated opening, and said elongated opening communicating with the exterior of said body;
   h. electrically conductive means extending from said auxiliary and reference electrodes within said elongated opening to the exterior of said body; and
   i. a cast insulating material filling void-free said annulus and elongated opening for integrally securing said tubular member, electrodes, electrically conductive means and body into a fluid-tight and rigid relationship, and said cast insulating material insulating said conductive means from each other in said body whereby said conductive means form circuits through said electrodes during conductivity measurements.

2. The conductivity probe of claim 1 wherein said electrodes are substantially identical ferrous members and the spacing between said auxiliary electrodes is greater than twice the spacing between one of the auxiliary electrodes and the reference electrode adjacent thereto.

3. The conductivity probe of claim 1 wherein said body is provided with a transverse opening intersecting said flow passage, and an insulating member is mounted in said transverse opening for movement within said flow passage between said auxiliary electrodes to position effecting the apparent conductivity constant for said probe provided by the cross-sectional area of said flux channel.

4. The conductivity probe of claim 3 wherein said insulating member is threadedly mounted in said transverse opening in said body for precise movement within said flow passage.

5. The conductivity probe of claim 3 wherein said insulating member is mounted in said transverse opening for movement transversely in said flow passage and substantially equidistant from said auxiliary electrodes.

6. A conductivity probe comprising:
   a. a body formed of a rigid insulating material and divided into two parts with a planar meeting surface, and said body having a cylindrical opening formed therein with the longitudinal axis of said opening residing along said planar meeting surface; and said cylindrical opening providing an insulating boundary defining a flux channel;
   b. adhesive means securing the parts of said body of said planar meeting surface into a leakproof interconnection;
   c. a pair of tubular members secured in fluid-tightness within said body and aligned coaxially of said cylindrical opening, said tubular members extending beyond said body and carrying end connections adapted to serve as inlet and outlet means for passing aqueous liquid through said flow passage;
   d. an elongated opening provided in said body and said elongated opening extending in said body at least partially the length of said cylindrical opening but separated therefrom by an imperforate wall of rigid insulating material, and said elongated opening communicating with the exterior of said body.

e. four metallic electrodes of elongated configuration disposed in the flow passage and mounted through said imperforate wall of said insulating material with at least one of their ends extending into said elongated opening, and said electrodes positioned in parallel relationship with their longitudinal axes transverse to said flow passage and residing in a plane containing the longitudinal axis of said flow passage;

f. one pair of said electrodes being auxiliary electrodes for providing current flow in said flow passage and another pair of said electrodes being reference electrodes serving as polarization potential monitors, said auxiliary electrodes residing adjacent one another and said reference electrodes residing remote from one another at the limits of said flux channel and adjacent each auxiliary electrode;

g. each of said reference electrodes spaced equidistant from the adjacent auxiliary electrode, and said auxiliary electrodes spaced apart a greater distance from one another than from said reference electrodes;

h. electrically conductive means extending from said auxiliary and reference electrodes within said elongated opening to the exterior of said body; and i. a cast insulating material filling said elongated opening in said body substantially void-free for integrally securing said electrodes, electrically conductive means and body into a fluid-tight and rigid relationship, and said cast insulating material insulating said conductive means from each other in said body whereby said conductive means form circuits through said electrodes during conductivity measurements.

7. The conductivity probe of claim 6 wherein said electrodes are substantially identical ferrous members and the spacing between said auxiliary electrodes is greater than twice the spacing between one of the auxiliary electrodes and the reference electrode adjacent thereto.

8. The conductivity probe of claim 6 wherein said body is provided with a transverse opening intersecting said flow passage and an insulating member is mounted in said transverse opening for movement within said flow passage between said auxiliary electrodes to position effecting the apparent conductivity constant for said probe provided by the cross-sectional area of said flux channel.

9. The conductivity probe of claim 8 wherein said insulating member is threadedly mounted in said transverse opening in said body for precise movement within said flow passage.

10. The conductivity probe of claim 8 wherein said insulating member is mounted in said transverse opening for movement transversely in said flow passage and substantially equidistant from said auxiliary electrodes.

* * * * *

UNITED STATES PATENT OFFICE
CERTIFICATE OF CORRECTION

PATENT NO. : 3,936,729

DATED : February 3, 1976

INVENTOR(S) : Joseph D. Winslow, Jr.

It is certified that error appears in the above-identified patent and that said Letters Patent are hereby corrected as shown below:

Column 2, line 57, for "aanother" read ---another---;

Column 4, line 32, for "memer" read -- member---;

Column 8, line 36, for "probe 52" read ---probe 51---;

lines 62-63, for "elelctrodes" read ---electrodes---;

Column 9, line 16, for "foreging" read ---foregoing---; and

Column 10, line 57, for "body of" read ---body at---.

Signed and Sealed this

Sixth Day of July 1976

[SEAL]

Attest:

RUTH C. MASON
*Attesting Officer*

C. MARSHALL DANN
*Commissioner of Patents and Trademarks*